(12) United States Patent
Bacon

(10) Patent No.: US 6,413,473 B1
(45) Date of Patent: Jul. 2, 2002

(54) MULTICOMPONENT TEST SYSTEMS USEFUL IN ANALYZING LIQUID SAMPLES, AND USES THEREFOR

(75) Inventor: Steven M. Bacon, Sparks, MD (US)

(73) Assignee: Taylor Technologies, Inc., Sparks, MD (US)

( * ) Notice: Subject to any disclaimer, the term of this patent is extended or adjusted under 35 U.S.C. 154(b) by 0 days.

(21) Appl. No.: 09/499,850

(22) Filed: Feb. 7, 2000

Related U.S. Application Data

(60) Provisional application No. 60/118,825, filed on Feb. 5, 1999.

(51) Int. Cl.[7] .............................................. G01N 21/78
(52) U.S. Cl. ........................... 422/56; 422/55; 422/61; 436/124; 436/125; 436/164; 436/166; 436/169
(58) Field of Search ................ 436/124, 125, 436/164, 166, 169; 422/56, 55, 61

(56) References Cited

U.S. PATENT DOCUMENTS

| | | |
|---|---|---|
| 3,910,764 A | 10/1975 | Tower |
| 3,964,831 A | 6/1976 | Frank |
| 4,129,417 A | 12/1978 | White |
| 4,195,059 A | 3/1980 | Whitcher et al. |
| 4,481,296 A | 11/1984 | Halley |
| 4,663,126 A | 5/1987 | Gould et al. |
| 4,904,605 A | 2/1990 | O'Brien et al. |
| 4,943,522 A | 7/1990 | Eisinger et al. |
| 5,073,484 A | 12/1991 | Swanson et al. |
| 5,145,789 A | * 9/1992 | Corti et al. .................. 436/530 |
| 5,268,146 A | 12/1993 | Lawrence et al. |
| 5,356,782 A | * 10/1994 | Moorman et al. ............ 422/56 |
| 5,491,094 A | 2/1996 | Ramana et al. |
| 5,529,751 A | 6/1996 | Gargas |
| 5,620,658 A | 4/1997 | Jaunakais |
| 5,710,372 A | 1/1998 | Becket |
| 5,811,254 A | 9/1998 | Wu |
| 5,972,294 A | * 10/1999 | Smith et al. .................. 422/58 |

* cited by examiner

Primary Examiner—Jill Warden
Assistant Examiner—LaToya Cross
(74) Attorney, Agent, or Firm—Fulbright & Jaworski L.L.P.

(57) ABSTRACT

The invention relates to multicomponent test systems which indicate the concentration of one or more analytes in a liquid sample, as well as the effect of action on the sample which results in an increase or decrease of the concentration of the analyte under consideration. Simulating increase or decrease permits the user to determine if corrective action is necessary, and what that corrective action might be. Both dry chemistry and wet chemistry systems are described.

24 Claims, 3 Drawing Sheets

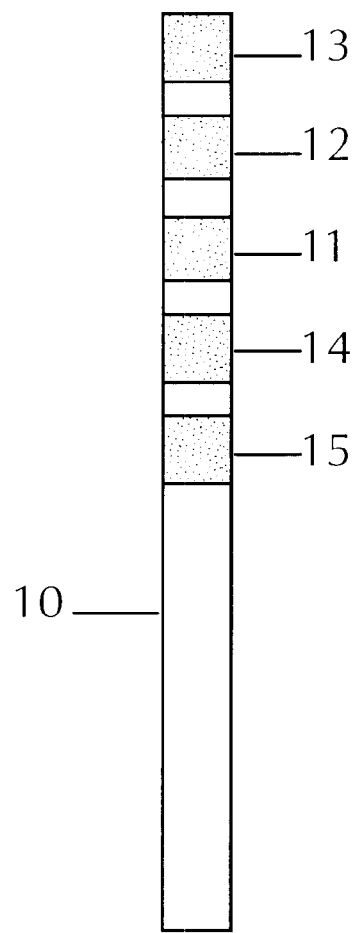
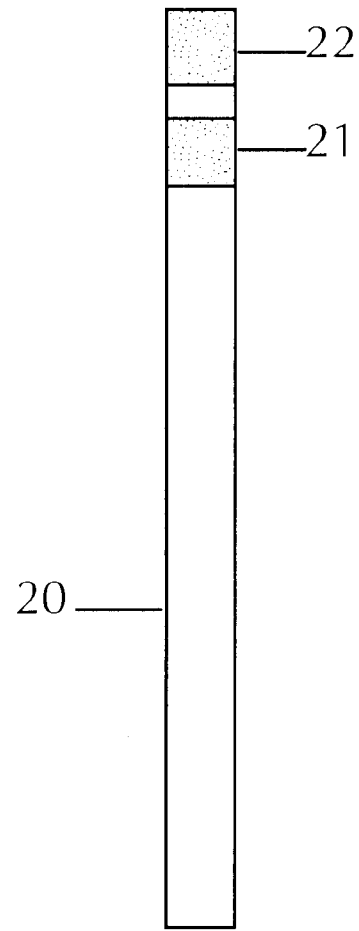
FIG. 1A  FIG. 1B

Important: All dosages are for 10,000 gallons of water. To find dosages for other volumes, use the following formula:

$$\frac{\text{Volume (gallons)}}{10,000} \times \text{Dosage per 10,000 gallons}$$

Directions for pH, TA, TH
1. Dip strip into water and immediately remove. Hold strip level. Do not shake off excess water.
2. Place strip between color standards and align pads with color standards from top to bottom.
3. Compare pads with color standards and select the pad whose color matches or falls between the color standards.
4. Read corresponding dosage.

Directions for FC
1. Dip strip into water and immediately remove. Hold strip level. Do not shake off excess water.
2. Place strip between color standards and align pads with color standards.
3. Compare pad with color standards.
4. Read corresponding dosage or corrective action.

FC
Target Range    Dosage (per 10,000 gallons) or Corrective Action
1    3
☐    ☐    FC=1 to 3
        None Required.

pH
Target Range

| 7.2 (<7.2 yellower) | 7.8 (>7.8 purpler) | Dosage (per 10,000 gallons) |
|---|---|---|
| ☐ | ☐ | Sodium Carbonate...1.6 lbs |
| ☐ | ☐ | Sodium Carbonate...15 oz |
| ☐ | ☐ | None Required |
| ☐ | ☐ | Sodium Bisulfate...12 oz |
| ☐ | ☐ | Sodium Bisulfate...2.3 lbs |

FC<1
*For Stabilized Pools*
Granular (68% chlorine)...3 oz
Tablet 1/4 oz (68% chlorine)...12-16
Tablet 1" (89% chlorine)...4
Tablet 3" (89% chlorine)...1
Stick (89% chlorine)...1
Capsule 10.5 oz (68% chlorine)...1
*For Non-Stabilized Pools*
Granular (68% chlorine)...6-8 oz
Tablet 1/4 oz (68% chlorine)...24-32
Capsule 10.5 oz (68% chlorine)...3

FC>3
Decrease daily feed.
Wait for level to drop to 3.

TA
Target Range

| 80 (<80 yellower) | 120 (>120 bluer) | Dosage (per 10,000 gallons) |
|---|---|---|
| ☐ | ☐ | Sodium Bicarbonate...14 lbs |
| ☐ | ☐ | Sodium Bicarbonate...7 lbs |
| ☐ | ☐ | None Required |
| ☐ | ☐ | Sodium Bisulfate...11 lbs |
| ☐ | ☐ | Sodium Bisulfate...22 lbs |

Directions for CC
1. Dip strip into water and immediately remove. Hold strip level. Do not shake off excess water.
2. Compare top pad with bottom pad.
3. Read corresponding dosage.

CC    Dosage (per 10,000 gallons)

Top pad<bottom pad
  None Required.
Top pad>bottom pad
  For Stabilized and Non-Stabilized pools
  Shock Treatment (68% chlorine)...1 lb
  Shock Treatment (75% chlorine)...13 oz

TH
Target Range

| 200 (<200 bluer) | 400 (>400 redder) | Dosage (per 10,000 gallons) |
|---|---|---|
| ☐ | ☐ | Calcium Chloride...21 lbs |
| ☐ | ☐ | None Required |
| ☐ | ☐ | Stain & Scale Control...1 qt |

FIG. 2

MULTICOMPONENT TEST SYSTEMS USEFUL IN ANALYZING LIQUID SAMPLES, AND USES THEREFOR

CROSS REFERENCE TO RELATED APPLICATIONS

This application claims priority of U.S. Provisional Application Serial No. 60/118,825, filed on Feb. 5, 1999, the disclosure of which is incorporated by reference in its entirety.

FIELD OF THE INVENTION

This invention relates to apparatus, methods, and reagents useful in analyzing liquid samples. More particularly, the invention relates to analyzing liquid samples to determine effect of a given amount of a given substance on the liquid sample. The invention is useful in, e.g., determining if a parameter of a liquid sample requires adjustment, and to what degree.

BACKGROUND AND PRIOR ART

The science of analytical chemistry has, and continues to make progress. The field involves the ability to assay sample materials to determine if a particular substance or substances are present, and if so, the amount of that substance. Frequently, the term "analyte" is used to describe the substance being tested. This term will be used hereafter.

Early examples of the application of analytical chemistry include litmus paper, as well as devices which would change color if atmospheric humidity was above a particular level. To say that the field has become more sophisticated since then is an understatement.

One area of importance in analytical chemistry is the testing and evaluation of liquid samples. While "liquid sample" as used hereafter refers to materials such as blood, urine, but most particularly for this disclosure, water.

It is desirable and necessary to analyze water for various components. For example, it may be important to determine if a water sample is potable. Further, water samples are used for different purposes. Depending upon the use to which the sample is to be put, one or more parameter, such as pH, total alkalinity, calcium hardness, total hardness, and amount of particular analytes such as total chlorine, free chlorine, combined chlorine, sodium content, etc., may be important. For example, when the water sample is taken from a swimming pool, either or both of combined chlorine and free chlorine may be important. Where the water is to be used for an industrial cooling system, total alkalinity or total hardness may be important. When the water is to be used in the health profession, any number of analytes may be of interest and important. These are just examples of the type of uses to which water samples may be put. The skilled artisan will be familiar with many others, which need not be set forth here. Further, the literature on analysis of liquid samples other than water is vast.

Analysis of water samples can be accomplished with any number of different systems. Generally, however, these systems can be divided into "dry chemistry" and "wet chemistry" systems.

In a wet chemistry system, essentially one adds either a liquid testing agent or a dissolvable testing agent to a liquid sample. The testing agent reacts with the analyte of interest, leading to formation of a detectable signal. Preferably, this is the formation of a visible "marker," such as a color or change in color. Again, the artisan will be familiar with other systems such as measurement of light absorption in photometers, etc. For purposes of this disclosure, however, the discussion will focus on visible formation and changes in color, rather than systems such as light photometers solely to facilitate understanding.

In these wet chemistry systems, the reacted liquid sample is then compared to some reference standard. Generally, this takes the form of a coded reference linking concentration of the analyte to a particular color or degree of color. A low concentration may be indicated by a very pale pink color, and a high concentration by one which is dark red, and vice versa.

Dry chemistry systems can be used to analyze many of the types of samples that wet chemistry systems are used to analyze. In these dry chemistry systems an apparatus, such as an absorbent pad or a test strip is impregnated, coated, or printed with the test system discussed supra, in such a way that the test system does not and cannot leave the apparatus. The apparatus is contacted with the liquid sample, removed from it, and signal is "read" on the apparatus. As with wet chemistry systems, the signal that is generated is compared to a coded reference to link the signal generated to a specific amount and/or concentration of an analyte under consideration.

The prior art literature on analytical chemistry is vast. For example, U.S. Pat. No. 5,811,254, to Wu, teaches reagent systems which can be used to detect total available chlorine over an extensive range (0 to 5000 ppm). The reagents can be incorporated into a carrier matrix, such as filter paper, to produce a dry chemistry test strip useful in measuring total available chlorine. U.S. Pat. No. 5,710,372, to Becket, teaches test strips which include a plurality of test regions. Each region contains a different amount of a reagent system which reacts with an analyte of interest. A visual display results which permits the user to determine the amount of the analyte in the sample being analyzed. U.S. Pat. No. 5,620,658, to Jaunakais, teaches multicomponent test strips which contain reagents capable of converting undetectable analytes into detectable ones, via ionic change. U.S. Pat. No. 5,529,751, to Gargas, teaches a pH adjustment kit. Once the pH of the sample has been determined, a first reagent is added until the sample indicates that a proper pH has been obtained. The number of drops of the first reagent is then converted to a quantity of a second reagent, which is then used to modify pH of the source of the sample. U.S. Pat. No. 5,491,094, to Ramana, et al., teaches dry reagent test strips for determining free chlorine, using TMB derivatives. U.S. Pat. No. 4,904,605, to O'Brien, et al., teaches test strips which can be used to determine a plurality of different reagents. A dipstick containing a plurality of reagent pads is contacted to sample, signal is formed, and then compared to a reference standard. U.S. Pat. No. 4,481,296, to Halley, teaches compositions that are useful in determining the pH of a halogen containing solution.

None of these references are believed to teach or suggest the invention described in this application, as explained hereafter.

Determination of an analyte and/or the amount of analyte in a sample, in many cases, is all that is of interest to a user of a reagent system. There are many cases, however, where such a determination is simply not sufficient. For example, with reference to the types of liquid samples described, the user needs to determine how to adjust a liquid sample so that the analyte concentration can be modified to a desired range. This can be necessary for any number of reasons, including user comfort, cost considerations, safety, and so forth. It is desirable to have analytical systems available which permit the user to not only determine the concentration of one or more analytes in a liquid sample, but also to determine what is necessary to modify the analyte concentration so that it falls within a desired range. It is especially desirable to be able to do this using a single analytical system.

Hence, it is a purpose of the invention described herein to provide a test system that is useful in determining both the amount of an analyte or analytes in a liquid sample, and to determine what would happen to the amount of a particular analyte in that sample, if a particular reactant or substance were added, in a defined amount.

It is also desirable to be able to accomplish the above, using a single apparatus. It is also desirable that the apparatus be simple to use, reliable, and inexpensive.

These aims as well as others which will be described, infra, are achieved via the invention which is described in the disclosure which follows.

BRIEF DESCRIPTION OF THE FIGURES

FIGS. 1A and 1B depict dry chemistry apparatus systems in accordance with the invention.

FIG. 2 shows a reference table useful in combination with a dry or wet chemistry system in accordance with the invention.

DETAILED DESCRIPTION OF PREFERRED EMBODIMENTS

Figure 3:
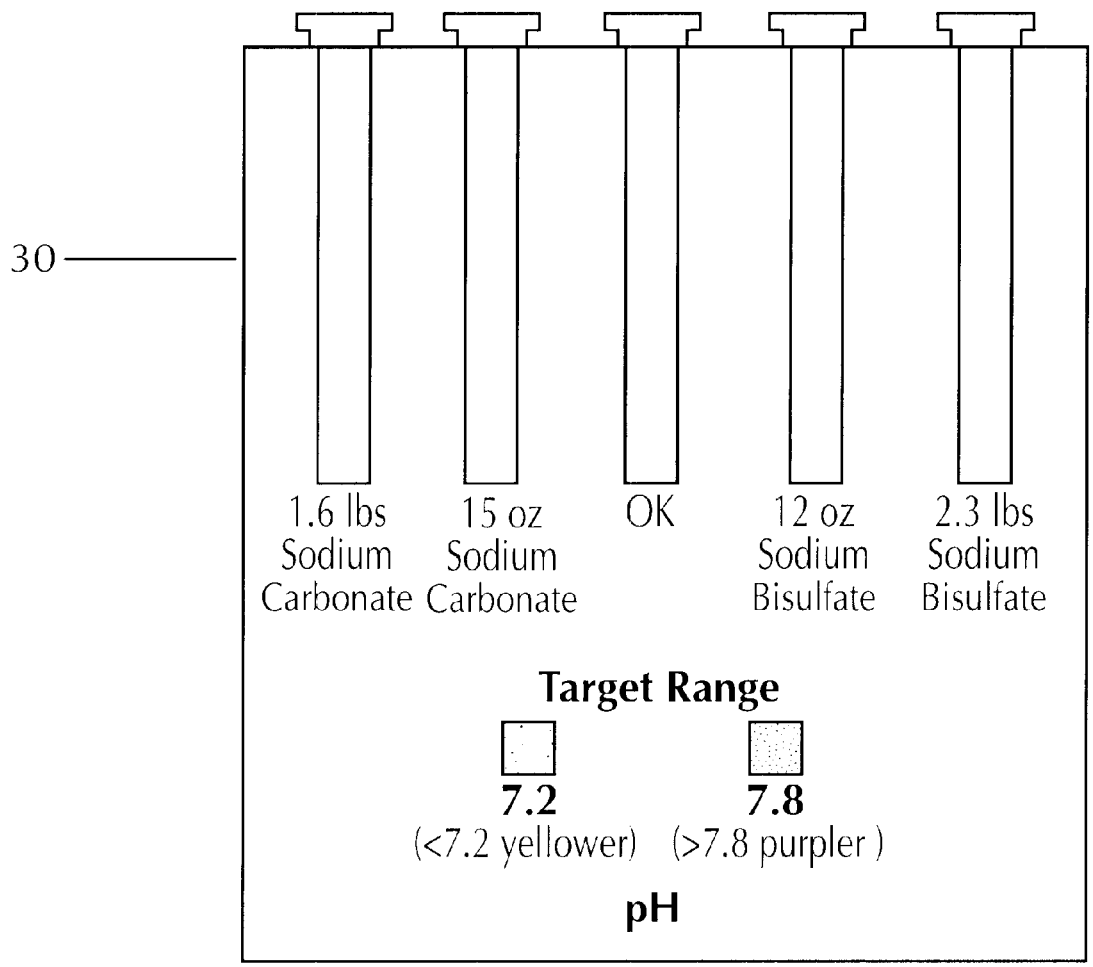
FIG. 3 shows a wet chemistry system in accordance with the invention.

In its broadest embodiment, the invention relates to a multicomponent reagent system, which is useful in determining both the concentration of a given analyte in a liquid sample, and the effect on this concentration of changing the amount of a given reactant present in the liquid sample. This is elaborated infra.

Features of the invention may be understood by considering a multicomponent reagent system designed to measure total alkalinity and how to modify it. In the invention described herein, a first reagent system is provided which is capable of determining total alkalinity in a liquid sample. Such reagent systems are well known, and include various indicators which provide a detectable signal, such as color, when the analyte of interest is present.

The second component of the system is one which is designed to determine the effect of changing the concentration of a given reactant in said liquid sample, by a defined amount, on the analyte of interest. With reference to total alkalinity, as discussed supra, if the liquid sample is one where there is concern that total alkalinity will be too low, the second component of the system is one which is designed to indicate the effect on total alkalinity by increasing the amount of an alkaline compound in said liquid sample by, e.g., 50 ppm. Hence, the second component contains this alkaline compound in an amount relative to the liquid sample of 50 ppm. When this second component is contacted with the liquid sample, a signal is generated which corresponds to "50 ppm+X," where "X" is the concentration of analyte in the sample. Conversely, if the liquid sample is one which tends to have a total alkalinity level greater than a desired range, the second component will be one which contains a reagent that lowers the concentration of the analyte by a given amount, such as 50 ppm. For example, again with reference to total alkalinity, it is known that acidic compounds react with, and neutralize alkaline substances, thus reducing total alkalinity. Hence, the second component may contain an acidic compound in an amount sufficient to decrease total alkalinity by 50 ppm. In this case, the first component of the system will register an analyte concentration at the top of, or beyond the scale of desirable concentrations, while the second component will indicate the effect of reducing the concentration. If the signal generated in the second component is within the range of desirable concentrations, then it can be concluded that an acidic substance, such as that included in the second component, should be added to the system. It will be understood, of course, that the second component of the system must contain the same reagents that are contained in the first component of the system, as well as at least one additional substance.

The skilled artisan will observe that while the invention only requires two components, three or more may be combined in one multicomponent system. There are situations where only a particularly narrow range of concentrations of an analyte are desirable or permissible, such as swimming pools. In these cases, it is not immediately evident that the source from which the liquid sample has been taken requires an increase or decrease in a particular analyte, such as chlorine. In these situations, the multicomponent reagent system will contain at least three separate systems, which determine (i) the concentration of the analyte, e.g., chlorine, (ii) the effect of adding a compound which acts to increase the concentration of the analyte, and (iii) the effect of adding a compound which acts to decrease the concentration of the analyte. Similarly, the multicomponent system of the invention may contain multiple reagent systems which indicate the effect of increasing and/or decreasing the concentration of an analyte by adding different concentrations of a compound. For example, with reference to a swimming pool and the analyte chlorine, described supra, one can envision a system using eleven different reagents. The first reagent, as always, is the reagent which determines if chlorine is present in the desired concentration, and then ten additional reagent systems, indicating the effect of increasing or decreasing chlorine concentration by 1, 2, 3, 4 and 5 parts per million. There is no maximum number of different, differentiated reagent systems which can be used. The skilled artisan will be able to determine routinely whether 2, 3, 5, etc., different systems are ideal for a given analytical test.

The multireagent system that is the invention may be used in liquid or dry form, but is most preferably configured in the form of a dry chemistry type apparatus, or a test strip. Referring to FIG. 1 of the drawings, this depicts two alternate forms of dry chemistry apparatus in accordance with the invention. FIG. 1A shows a test strip 10, which includes a solid, inert backing material or support, onto which are attached five separate test pads which are separated from each other. Test pad 11 is the first component of the multiple reagent system as described supra. It contains a reagent system which, upon reaction with an analyte, yields a detectable signal indicative of a concentration or range of concentrations for the analyte. Particular analyte/reagent systems are described, infra. The remaining test pads, i.e., 12, 13, 14 and 15, sometimes referred to as "treatment pads" contain reagents which indicate the effect on changes on the concentration of analyte of interest, when a compound is added that changes the concentration of analyte by a predetermined amount. The pads represented by "12" and "14" may indicate, e.g., the effect of reagents which increase and decrease, respectively, the concentration of analyte by 50 ppm, while "13" and "15" may represent the effect of reagents which increase and decrease, respectively, analyte concentration by 100 ppm. It will be clear that the pads may be arranged in any order that is convenient to the end user.

FIG. 1B depicts another embodiment of the invention, which is useful in, e.g., determining if an analyte in a sample exceeds a defined amount or concentration. In FIG. 1B a test strip "20" is depicted, which includes two reagent pads "21" and "22." The first reagent pad "21" contains reagents which will provide a signal indicative of a predefined amount of a form of an analyte of interest. It also contains a reagent system which reacts with different or related forms of the analyte, such that the signal generated in the reagent pad is the sum of a predefined value, plus one variable. Reagent pad "22", in contrast, contains reagents which will react with and provide a signal indicative of all forms of the analyte. If there are two forms of the analyte under consideration, then two variables are under consideration, and reagent pad "22" provides a signal indicative of the sum of these concentrations. An embodiment of this type is especially useful in determining, e.g., the amount of combined chlorine in a sample, as will be explained, infra.

FIG. 2 shows a device which is useful in connection with the device shown in, e.g., FIG. 1. To elaborate, consider FIG. 1A configured so that "13" indicates the effect of increasing total alkalinity by a large amount, while "12" represents the effect of increasing it by a smaller amount, such as half the amount provided by "13." Continuing down the device, "11" represents the portion of the apparatus which depicts actual concentration in the sample, while "14" represents a small decrease in total alkalinity, and "15" represents a larger decrease. In practice, this test device is dipped into a sample of water, and the color in the various components is allowed to develop. Once this occurs, the test device is compared to the "TA" portion of FIG. 2. This device presents preprinted colors indicative of what is a target range for the analyte. In this case, the target range for total alkalinity is, as noted, 80–120 ppm. One aligns the five, developed colors on the device of FIG. 1A to the target range colors printed in FIG. 2. Each of these, as will be seen, correlates to a set of instructions provided in the appropriate portion of FIG. 2. In the case of total alkalinity, for example, if the color formed in "13" is found to correlate to the printed colors of the target range, this indicates to the user that the total alkalinity concentration in the water is very low, and action must be taken to increase it, as indicated in the instructions connected to "Sodium Bicarbonate . . . 14 lbs." In contrast, if the color that develops in "15" of FIG. 1A correlates to the target range, this indicates that the concentration, i.e., the total alkalinity in the water is too high, and must be decreased by adding, for example, 22 pounds of sodium bisulfate.

In the embodiment shown in FIG. 2, other components beside total alkalinity can be assayed. The figure shows how to carry out similar analyses for, e.g., "pH," "FC" or "free chlorine," "TH" or "total hardness," and "CC" or "combined chlorine." Each of these different analytes may be measured separately, in an individual test strip, and various combinations, such as free chlorine and combined chlorine can be measured on one apparatus.

FIG. 3 shows one embodiment of a wet chemistry type of system in accordance with the invention. In this system, a first reagent system is provided for determining the actual concentration of analyte in a sample. The remaining vials hold either liquid forms of a second reagent system which includes, e.g., a sodium carbonate solution, or a dry form of the second reagent system which is solubilized upon contact with sample. The compound reacts with the analyte in the sample, and forms a detectable signal such as color, which is then compared to the color printed for the target range. The system depicted in FIG. 3 determines pH, in a system where a target range of 7.2–7.8 is appropriate. Hence, the system is provided with preprinted color boxes for the endpoints of this range. If a sample vial exhibits the same color as the target range, this indicates that treatment with the particular reagent in the given amount is expected to result in an analyte concentration in a desired, or target range. Further, if the color formed in the "OK" vial correlates to the printed colors, it indicates that no action is necessary. Other analytes can be determined in similar fashion.

A further aspect of the invention are reagent systems, apparatus in particular, which are useful in determining if a particular type of analyte is present above a defined amount. Such a system is useful when problems arise when the defined amount is exceeded. Reference will be made herein to chlorine as it is present in swimming pools, but the principles discussed herein will be understood by the skilled artisan to apply to analytes other than chlorine, in liquid samples other than swimming pools.

"Total chlorine" or "TC", as used herein, refers to the sum of free chlorine or "FC" in a liquid sample, plus combined chlorine or "CC". In other words:

$$TC = FC + CC$$

FC represents the amount of chlorine present from HOCl and OCl in a liquid sample. CC indicates the amount of chlorine that has combined with nitrogenous compounds, such as ammonia based waste products, to form chloramines. CCs are problematic in swimming pools, leading to unpleasant odors, irritation of mucous membranes, and so forth.

It is generally accepted that a CC level of above about 0.3 ppm leads to irritation and odor. To determine if this level has been exceeded, an apparatus in accordance with the invention includes a first reagent pad, which contains a reagent system that is capable of measuring total chlorine in a liquid sample, determinable via a color change or formation in the sample. The apparatus also contains a second reagent pad which contains a reagent system that will measure the FC value and which also contains a reagent system that simulates 0.3 ppm of CC. In other words, this second system will provide a signal indicative of 0.3 ppm of CC regardless of whether or not there is any chlorine in the sample whatsoever. The color of this second reagent pad will thus be indicative of 0.3 ppm of CC plus whatever the amount of FC is present in the sample. The first reagent pad, referred to supra, will give a signal indicative of TC in the sample, i.e., FC plus CC.

Since both reagent pads measure the FC in the same sample, the single variable is the portion of the signal generated by the first reagent pad attributable to the CC value in the sample. Since the reagents used in the first pad are chosen to be equivalent to or the same as those in the second reagent pad, visual inspection of the two pads permits the user to determine if the CC level exceeds 0.3 ppm. Essentially, if the signal generated in the first reagent pad is stronger than that generated by the second reagent pad, then the CC level in the sample is above the threshold value, and the sample source must be treated to reduce the level. On the other hand, if the signal in the first reagent pad is not as intense as the signal for the second reagent pad, then one can assume the concentration of CC is within acceptable limits.

With reference to FIG. 2, supra, again one sees in the "Directions for CC" an explanation of what action is necessary if the combined chlorine value exceeds the defined, or reference value.

It is to be understood that the value of 0.3 ppm is one choice available, and, the reagent pads can be designed such that the simulated value in what is referred to as the second reagent pad can vary. Further, chlorine is exemplary of any number of analytes which can be quantified in the same way, in any type of liquid sample.

In all embodiments of the invention as described herein, various options are available to the skilled artisan with respect to the reagent systems employed. In a test apparatus such as the one shown in FIG. 1A, a particular reagent system is present in reagent pad "11", and is capable of indicating the concentration of an analyte under consideration. This reagent system should also be present in each of reagent or treatment pads 12, 13, 14 and 15. These reagent pads should also include an additional reagent system. With respect to those reagent pads which are to indicate an increase in analyte concentration, various options are available to the artisan. Each pad can include, for example, a preformed dye in an amount indicative of the increase to be shown. For example, one pad can contain an amount of preformed dye indicative of 50 ppm of TA, and the other can include preformed dye indicative of 100 ppm of TA. These pads also include the reagent system incorporated into pad 11 and, when the sample contacts these pads, the resulting signal is the sum of the preformed dye plus the signal generated by reaction of analyte with the reagent system.

Alternatively, the reagent pads can contain a second reagent system (the reagent system used in, e.g., reagent pad 11 is the first reagent system), which either indicates or simulates the effect of a particular component on the sample. To elaborate, there are situations where it is feasible and desirable to include, in the reagent pad, the actual component which would be added to the liquid sample to effect the change. There are cases, however, where a component that will be used in the liquid sample does not lend itself to incorporation into a dry test strip. In such cases, a different material may be incorporated into the dry reagent pad, as long as the concentration included therein is equivalent to an amount of actual component which is then indicated to be corrective. This is what is meant herein when reference is made to simulating effect of a component.

It must also be recognized that when "change" is used herein, it may, but need not necessarily refer to the addition of a particular component to a liquid sample. Change may be effected by mechanical means, such as by changing feed rates on automatic or passive systems which control flow in and out of the sample, and so forth.

The invention will become clearer via the representative examples which follow.

EXAMPLE 1

A test system was prepared that was designed to measure total alkalinity of a liquid sample, as well as the effect of adding various components to the liquid so as to decrease or increase total alkalinity. An indicator reagent was prepared from a 0.1% solution of the sodium salt of BCG, and 0.0035 M citrate buffer. These were combined in a ratio of 1.5 to 1 (e.g. 7.5 ml citrate buffer, and 5 ml of indicator solution). This served as the system which measured a target range of total alkalinity in a sample. In the experiments described herein, total alkalinity is described in terms of $CaCO_3$. This is the industry standard.

A reagent system was prepared which would reduce the total alkalinity of the solution by 100 ppm. This reagent was prepared by adding 0.05 ml of 0.6 M citric acid to 10 ml of the indicator system. A reagent which reduced TA by 50 ppm was prepared by adding 0.025 ml of 0.6 M citric acid to 10 ml of the indicator system. In parallel, a reagent which increased TA by 50 ppm was prepared by adding 0.0215 ml of 0.6 N $NaHCO_3$ solution to 10 ml of the indicator system, and one which increased TA by 100 ppm was prepared by adding 0.043 ml of 0.6 N $NaHCO_3$ to 10 ml of the indicator system.

Individual test pads were made by impregnating one of the five reagents described supra onto absorbent Whatman Grade 31 ET paper.

Standard total alkalinity solutions were made by dissolving differing amounts of $Na_2CO_3$ or $NaHCO_3$, to prepare solutions containing 0, 20, 30, 40, 50, 70, 80, 100, 120, 130, 140 150, 170, 190 and 240 ppm TA. Pads were dipped into each of these solutions, and color was allowed to develop. Pads were matched, depending upon the color formed.

The pads impregnated with indicator system only yielded detectable signals. These correlated universally with the test pads. In other words, the color formed in a test pad impregnated with indicator only and dipped into a 30 ppm solution was a good match for the color formed when a pad impregnated with the solution designed to simulate a decrease of 100 ppm was dipped into a solution of 130 ppm TA. Similarly, a test pad impregnated with indicator only and dipped into a solution with TA of 140 ppm formed a color that was a good match for the color formed by a test pad impregnated with a reagent designed to simulate a 100 ppm increase that was dipped into a solution of 40 ppm TA. This pattern was observed across the board.

EXAMPLE 2

The results in example 1 were followed by construction of an embodiment of the invention of the type shown in FIG. 1, i.e., a treatment strip with five separate pads, each of which was impregnated with one of the reagents described in example 1. The pads were then dipped into solution of tap water and $NaHCO_3$, at 60, 120, 160, and 240 ppm. The results follow:

| 5 PAD TREATMENT STRIP | TA OF SAMPLE | RESULTS |
| --- | --- | --- |
| +100 | 60 | 160 |
| +50 | 60 | 110 |
| 0 | 60 | 60 |
| −50 | 60 | 10 |
| −100 | 60 | 0 |
| +100 | 120 | 220 |
| +50 | 120 | 170 |
| 0 | 120 | 120 |
| −50 | 120 | 70 |
| −100 | 120 | 20 |
| +100 | 160 | 260 |
| +50 | 160 | 210 |
| 0 | 160 | 160 |
| −50 | 160 | 110 |
| −100 | 160 | 60 |
| +100 | 240 | >240 |
| +50 | 240 | >240 |
| 0 | 240 | 240 |
| −50 | 240 | 190 |
| −100 | 240 | 140 |

These results showed, conclusively, that the treatment pad concept was viable. Specifically, the reagents necessary for carrying out the type of assay described, supra, could be incorporated into a dry chemistry apparatus, with successful results.

EXAMPLE 3

This example details the preparation of a further embodiment of an apparatus in accordance with the test invention.

In order to measure free chlorine only, a first set of reagent pads were dipped into an indicator solution of N,N-diethyl-p-phenylenediamine ("DPD" hereafter) and phosphate buffer. A second set of reagent pads were dipped into the solution of DPD, together with a dye solution. The dye solution was formulated to simulate the color formed when a test pad, containing indicator, had been dipped into a solution containing 2 ppm of free chlorine. All test pads consisted of Whatman 31 ET paper and were dried at 40° C.

Pads were then dipped into solutions containing different concentrations of free chlorine, and then compared to each other.

Generally, the color formed on pads containing the indicator and the dye were equivalent to the color formed on the pads containing indicator alone, when tested on solutions containing 2 ppm more of free chlorine. In other words, the color formed when a test pad containing indicator and dye was dipped into a solution containing 0 ppm free chlorine was equivalent to the color formed when a test pad, containing only indicator, was dipped into a 2 ppm solution of free chlorine.

EXAMPLE 4

These experiments parallel those set forth in example 3, supra, somewhat, except that in these experiments, solutions of indicator, were admixed with solutions of sodium thiosulfate to decrease free chlorine in a sample. A 0.030 ml solution of $Na_2S_2O_3$ was combined with the indicator, and test pads were dipped into this solution. The test pads again consisted of Whatman 31 ET paper, and were dried at 40° C. In parallel, test pads were made which contained indicator only. Pads were dipped into solutions containing varying concentrations of free chlorine, and colors compared.

The pads dipped into indicator plus $Na_2S_2O_3$ formed colors with solutions containing free chlorine. They were equivalent to color developed with pads containing indicator only that were dipped into solutions containing about 2.5–3 ppm less free chlorine. In other words, a test pad containing indicator and $Na_2S_2O_3$ developed a color with a 3 ppm solution of free chlorine comparable to one developed in a test pad containing only indicator, at 0 ppm free chlorine.

EXAMPLE 5

This example details the manufacture of multicomponent dry chemistry test strips useful in determining pH and the effect of decreasing pH with acid.

Phenol red is an acid-base indicator known to undergo color changes at a pH of from about 6.4 to 8.0. See, e.g., U.S. Pat. No. 4,481,296. This known compound was used to formulate multicomponent test strips, for analysis of pH.

Reagent pads were prepared for analysis of pH in a liquid sample, by incorporating a 0.025% solution of the sodium salt of phenol red into a pad, together with surfactant. The pads were allowed to dry, at 75° C. for 30 minutes.

Treated pads were prepared by contacting reagent pads with the same solution of phenol red, as well as varying amounts of a 1N solution of sulfuric acid (0.033, 0.067, 0.100, 0.133 ml), and dried. The reagent pads were then tested in sodium bicarbonate/sodium carbonate solutions of varying pH, which had been tested prior to the analysis with the test pads. The results follow, in terms of the amount of 1N sulfuric acid solution included in the pad.

| $1N\ H_2SO_4$ (ml) | 0 | 0.033 | 0.067 | 0.100 | 0.133 |
|---|---|---|---|---|---|
| Solution pH: 8.14 (100 ppm TOTAL ALKALINITY AS $CaCO_3$) | | | | | |
| pH of pad | 7.8–8.2 | 7.5 | 7.2 | 6.8–7.2 | 6.8 |
| Solution pH: 8.19 (130 ppm TOTAL ALKALINITY AS $CaCO_3$) | | | | | |
| pH of pad | 7.8–8.2 | 7.5–7.8 | 7.5 | 7.2–7.5 | 6.8–7.2 |
| Solution pH: 8.19 (180 ppm TOTAL ALKALINITY AS $CaCO_3$) | | | | | |
| pH of pad | 7.8–8.2 | 7.5–7.8 | 7.5 | 7.2–7.5 | 6.8–7.2 |
| Solution pH: 8.20 (200 ppm TOTAL ALKALINITY AS $CaCO_3$) | | | | | |
| pH of pad | 7.8–8.2 | 7.8 | 7.5 | 7.3 | 7.2 |
| Solution pH: 8.25 (220 ppm TOTAL ALKALINITY AS $CaCO_3$) | | | | | |
| pH of pad | 8.2 | 7.8–8.2 | 7.5 | 7.2–7.5 | 7.2 |
| Solution pH: 8.27 (260 ppm TOTAL ALKALINITY AS $CaCO_3$) | | | | | |
| pH of pad | >8.2 | 7.8–8.2 | 7.8–8.2 | 7.5–7.8 | 7.5 |

This indicates that a multicomponent test strip can be prepared which indicates the effect of decreasing pH with acid of varying total alkalinity concentrations in a water sample.

EXAMPLE 6

Example 5, supra, detailed manufacture of multicomponent dry chemistry test strips useful in determining pH and the effect of lowering pH with acid. This example shows a similar system, designed to show the effect of increasing pH with alkali.

Reagent pads were prepared as described supra. Treatment pads were prepared as described supra as well, except that varying amounts of 1N sodium carbonate solution (0.0083, 0.0167, 0.025, 0.033 ml) were used, instead of 1N sulfuric acid. Reagent pads were tested in sodium bicarbonate/sodium carbonate solutions at varying pH, which had been tested prior to analysis with the reagent pads. Results follow, in terms of the amount of 1N sodium carbonate solution in the reagent pad.

| 1N Sodium Carbonate (ml) | 0 | 0.0083 | 0.0167 | 0.025 | 0.033 |
|---|---|---|---|---|---|
| Solution pH: 6.99 (80 ppm TOTAL ALKALINITY AS $CaCO_3$) | | | | | |
| pH of pad | 6.8–7.2 | 7.2–7.5 | 7.5–7.8 | >8.2 | >8.2 |
| Solution pH: 6.83 (70 ppm TOTAL ALKALINITY AS $CaCO_3$) | | | | | |
| pH of pad | 6.8 | 7.2 | 7.5 | >8.2 | >8.2 |
| Solution pH: 6.54 (60 ppm TOTAL ALKALINITY AS $CaCO_3$) | | | | | |
| pH ofpad | <6.8 | 7.2–7.5 | 7.5–7.8 | >8.2 | >8.2 |
| Solution pH: 6.92 (170 ppm TOTAL ALKALINITY AS $CaCO_3$) | | | | | |
| pH of pad | 6.8–7.2 | 7.2–7.5 | 7.5–7.8 | >8.2 | >8.2 |
| Solution pH: 6.69 (160 ppm TOTAL ALKALINITY AS $CaCO_3$) | | | | | |
| pH of pad | <6.8 | 7.2–7.5 | 7.5–7.8 | >8.2 | >8.2 |
| Solution pH: 6.46 (130 ppm TOTAL ALKALINITY AS $CaCO_3$) | | | | | |
| pH of pad | <6.8 | 6.8–7.2 | 7.2–7.5 | >8.2 | >8.2 |

This example indicates that a multicomponent test strip can be prepared which indicates the effect of increasing pH with alkali at varying concentrations of total alkalinity in a water sample.

EXAMPLE 7

This example details work on the preparation of a total hardness treatment strip. An indicator pad was made by dipping an absorbent pad into a solution of 4.5 ml phosphate buffer (pH6), 3.4 ml EDTA (0.12N)(pH 8.5), and 8.8 ml hydroxynaphthol blue, diluted with distilled water. Test pads were then prepared with increased hardness by adding 2.0 ml 0.02 N $CaCO_3$ (increases by 100 ppm), or 4.0 ml of 0.02 N $CaCO_3$ (increases by 200 ppm). Test pads with decreased hardness were prepared by increasing EDTA to 5.8 ml (decreases $CaCO_3$ by 200 ppm), and 8.1 ml (decreases $CaCO_3$ by 400 ppm). Hence, pads calibrated to +200, +100, 0, −200, and −400 were prepared. These five reagent pads were then tested with solutions having total hardness of 0, 100, 600, and 700. Pads were dipped into the solution, and colors formed were compared to standards developed for solutions with varying degrees of total hardness. The results are set forth infra.

| | | TH CONCENTRATION OF SAMPLE (IN PPM) | | | | | |
|---|---|---|---|---|---|---|---|
| 0 | | 100 | | 600 | | 700 | |
| Pad | Result | Pad | Result | Pad | Result | Pad | Result |
| +200 | 200 | +200 | 300 | +200 | >700 | +200 | >700 |
| +100 | 100 | +100 | 200 | +100 | 700 | +100 | >700 |
| 0 | 0 | 0 | 100 | 0 | 600 | 0 | 700 |
| −200 | 0 | −200 | 0 | −200 | 400 | −200 | 500 |
| −400 | 0 | −400 | 0 | −400 | 200 | −400 | 300 |

It is generally accepted that the target range for TH in a swimming pool water sample is 200–400 ppm $CaCO_3$. Analysis of these results tells the user that, for the first solution, only a pad which simulates an increase by 200 ppm puts the solution in the target range. For the second solution, at 100 ppm, the results advise that an increase of at least 100 ppm is desirable. For the solution at 600 ppm, the results indicate that the pads which simulate decrease of 200 and 400 ppm will put the solution in the target range, while the solution at 700 ppm gives results which indicate that only a drastic reduction of 400 ppm will place the sample source in the target range.

The examples which follow are wet chemistry embodiments of the invention, designed to determine the effect of varying alkalinity on the amount of acid and base required to bring pH into the range of 7.2–7.6.

EXAMPLE 8

To a 10 ml water sample having a pH of 6.6 and a TA of 35–40 was added 0.5 ml of phenol red indicator. Table 1 summarizes the results of treatments ranging from one to five drops of acid demand (AD) ($0.02NH_2SO_4$) and base demand (BD) ($0.02N\ Na_2CO_3$) each, as well as no treatment.

TABLE 1

| | pH 6.6 and Total Alkalinity 35–40 ppm as $CaCO_3$ | | | | | | | | | | |
|---|---|---|---|---|---|---|---|---|---|---|---|
| | 5 BD | 4 BD | 3 BD | 2 BD | 1 BD | 0 | 1 AD | 2 AD | 3 AD | 4 AD | 5 AD |
| pH | >7.6 | 7.4 | 7.2 | <7.2 | <7.2 | 6.6 | <6.6 | <6.6 | <6.6 | <6.6 | <6.6 |
| Color | * | R | R | (7.1) | (6.9) | * | * | * | * | * | * |

As can be seen from Table 1, for a pH of 6.6 and a TA of 35–40, either three or four drops of base demand will raise the pH of the sample to within the target range.

EXAMPLE 9

To a 10 ml water sample having a pH of 7.0 and a TA of 35–40 was added 0.5 ml of phenol red indicator. Table 2 summarizes the results of the treatments as described in Example 8.

TABLE 2

| | pH 7.0 and Total Alkalinity 35–40 ppm as $CaCO_3$ | | | | | | | | | | |
|---|---|---|---|---|---|---|---|---|---|---|---|
| | 5 BD | 4 BD | 3 BD | 2 BD | 1 BD | 0 | 1 AD | 2 AD | 3 AD | 4 AD | 5 AD |
| pH | >7.6 | >7.6 | >7.6 | 7.4 | 7.2 | 7.0 | <7.0 | <7.0 | <7.0 | <7.0 | <7.0 |
| Color | (8.2) | (8.0) | (7.7) | R | R | * | * | * | * | * | * |

Thus, for a pH of 7.0 and a TA of 35–40, either one or two drops of base demand will raise the pH to within the target range.

EXAMPLE 10

To a 10 ml water sample having a pH of 7.4 and a TA of 35–40 was added 0.5 ml of phenol red indicator. Table 3 summarizes the results of the treatments as described in Example 8.

TABLE 3

| pH 7.4 and Total Alkalinity 35–40 ppm as CaCO$_3$ | | | | | | | | | | |
|---|---|---|---|---|---|---|---|---|---|---|
| | 5 BD | 4 BD | 3 BD | 2 BD | 1 BD | 0 | 1 AD | 2 AD | 3 AD | 4 AD | 5 AD |
| pH | >7.6 | >7.6 | >7.6 | >7.6 | 7.6 | 7.4 | 7.0 | <7.0 | <7.0 | <7.0 | <7.0 |
| Color | (8.2) | (8.2) | (8.0) | (7.8) | R | R | * | * | * | * | * |

Thus, for a pH of 7.4 and a TA of 35–40, one drop of base demand will yield a pH within the target range, and since the pH is already within range, a "zero treatment" also yields a pH (7.4) within target range.

EXAMPLE 11

To a 10 ml water sample having a pH of 7.6 and a TA of 40 was added 0.5 ml of phenol red indicator. Table 4 summarizes the results of the treatments as described in Example 8.

TABLE 4

| pH 7.6 and Total Alkalinity 40 ppm as CaCO$_3$ | | | | | | | | | | |
|---|---|---|---|---|---|---|---|---|---|---|
| | 5 BD | 4 BD | 3 BD | 2 BD | 1 BD | 0 | 1 AD | 2 AD | 3 AD | 4 AD | 5 AD |
| pH | >7.6 | >7.6 | >7.6 | >7.6 | 8.0 | 7.6 | 7.1 | <7.0 | <7.0 | <7.0 | <7.0 |
| Color | * | * | * | (8.2) | * | R | (<7.2) | * | * | * | * |

For a pH of 7.6 and a TA of 40, no treatment is necessary since the pH is already in range. One drop of acid demand yielded a pH very close to, but below, the lower endpoint of the target range (7.2).

EXAMPLE 12

To a 10 ml water sample having a pH of 6.5 and a TA of 60 was added 0.5 ml of phenol red indicator. Table 5 summarizes the results of the treatments as described in Example 8.

TABLE 5

| pH 6.5 and Total Alkalinity 60 ppm as CaCO$_3$ | | | | | | | | | | |
|---|---|---|---|---|---|---|---|---|---|---|
| | 5 BD | 4 BD | 3 BD | 2 BD | 1 BD | 0 | 1 AD | 2 AD | 3 AD | 4 AD | 5 AD |
| pH | >6.5 | >6.5 | >6.5 | >6.5 | >6.5 | 6.5 | <6.5 | <6.5 | <6.5 | <6.5 | <6.5 |
| Color | * | * | * | * | * | * | * | * | * | * | * |

This experiment revealed that more base demand is required at lower pH values to raise the pH into the target range.

Experiments next were run to determine whether a five (5)-pad treatment strip or five (5) compartment liquid system would be effective over a broad range of pH and TA values. Each 10 ml water sample contained 0.435 ml of phenol red indicator. The acid tests included one and three drops of acid demand (0.02N H$_2$SO$_4$), respectively, and the base tests included three and five drops of base demand (0.02N Na$_2$CO$_3$), respectively.

EXAMPLE 13

A sample having a TA of 90, a pH of 8.56, and a total dissolved solids (TDS) of 87 was tested with the five (5)-component system described above. The results are summarized in Table 6.

TABLE 6

| pH 8.56 and Total Alkalinity 90 ppm as CaCO$_3$ | | | | | |
|---|---|---|---|---|---|
| | 5 BD | 3 BD | 0 | 1 AD | 3 AD |
| pH | >8 | >8 | 8.1 | 7.6 | 7.0 |
| Color | (8.2) | (8.2) | * | R | * |

As is apparent from Table 6, one drop of acid demand was effective for lowering pH of the sample to a value within the target range.

EXAMPLE 14

A sample having a TA of 90, a pH of 8.45, and a TDS of 667 was tested with the five (5)-component system described above. The results are summarized in Table 7 below.

TABLE 7

| pH 8.45 and Total Alkalinity 90 ppm as CaCO$_3$ | | | | | |
|---|---|---|---|---|---|
| | 5 BD | 3 BD | 0 | 1 AD | 3 AD |
| pH | >8 | >8 | 8.1 | 7.6 | 7.0 |
| Color | (8.2) | (8.2) | * | R | * |

As is apparent from Table 7, one drop of acid demand was effective for lowering pH of the sample to a value within the target range.

EXAMPLE 15

A sample having a TA of 120, a pH of 8.37, and a TDS of 713 was tested with the five (5)-component system described above. The results are summarized in Table 8 below.

TABLE 8

| pH 8.37 and Total Alkalinity 90 ppm as $CaCO_3$ | | | | |
|---|---|---|---|---|
| 5 BD | 3 BD | 0 | 1 AD | 3 AD |
| pH >8 | >8 | 8.1 | 7.7 | 7.2 |
| Color (8.2) | (8.2) | * | * | R |

As is apparent from Table 8, three drops of acid demand were effective for lowering pH of the sample to value within the target range.

EXAMPLE 16

A sample having a TA of 150, a pH of 8.35, and a TDS of 707 was tested with the five (5)-component system described above. The results are summarized in Table 9 below.

TABLE 9

| pH 8.35 and Total Alkalinity 150 ppm as $CaCO_3$ | | | | |
|---|---|---|---|---|
| 5 BD | 3 BD | 0 | 1 AD | 3 AD |
| pH >8 | >8 | 8.1 | 7.7 | 7.3 |
| Color (8.2) | (8.2) | * | * | R |

Thus, three drops of acid demand were effective for lowering pH of the sample to a value within the target range.

EXAMPLE 17

A sample having a TA of 200, a pH of 8.34, and a TDS of 740 was tested with the five (5)-component system described above. The results are summarized in Table 10 below.

TABLE 10

| pH 8.34 and Total Alkalinity 200 ppm as $CaCO_3$ | | | | |
|---|---|---|---|---|
| 5 BD | 3 BD | 0 | 1 AD | 3 AD |
| pH >8 | >8 | 8.1 | 7.8 | 7.4 |
| Color (8.2) | (8.2) | * | * | R |

As can be seen from Table 10, three drops of acid demand were effective for lowering pH of the sample to a value within the target range.

EXAMPLE 18

A sample having a TA of 260, a pH of 8.36, and a TDS of 813 was tested with the five (5)-component system described above. The results are summarized in Table 11 below.

TABLE 11

| pH 8.36 and Total Alkalinity 260 ppm as $CaCO_3$ | | | | |
|---|---|---|---|---|
| 5 BD | 3 BD | 0 | 1 AD | 3 AD |
| pH >8 | >8 | 8.1 | 7.9 | 7.6 |
| Color (8.2) | (8.2) | * | * | R |

Three drops of acid demand were effective for lowering pH of the sample to a value within the target range.

EXAMPLE 19

The TA of the sample of Example 18 was lowered to 210 using HCl. The pH was measured as 6.93, and TDS as 800. The sample was tested with the five (5)-component systems described above. The results are summarized in Table 12 below.

TABLE 12

| pH 6.93 and Total Alkalinity 210 ppm as $CaCO_3$ | | | | |
|---|---|---|---|---|
| 5 BD | 3 BD | 0 | 1 AD | 3 AD |
| pH 7.1 | 7.0 | <7.0 | <7.0 | <7.0 |
| Color * | * | (6.9) | (6.8) | (6.7) |

Seven additional drops of base demand were required (12 altogether) to yield a pH of 7.2, within the target range.

EXAMPLE 20

The TA of the sample of Example 19 was lowered to 110 using HCl. The pH was measured as 6.48, and TDS as 800. The sample was tested with the five (5)-component system described above. The results are summarized in Table 13 below.

TABLE 13

| pH 6.48 and Total Alkalinity 110 ppm as $CaCO_3$ | | | | |
|---|---|---|---|---|
| 5 BD | 3 BD | 0 | 1 AD | 3 AD |
| pH <7.0 | <7.0 | <7.0 | <7.0 | <7.0 |
| Color * | * | * | * | * |

Fourteen additional drops of base demand were required (19 altogether) to yield a pH of 7.2, within the target range.

EXAMPLE 21

Next, samples having low pH and low initial concentration of $NaHCO_3$ were tested with the two base demand treatments (the acid demand treatment was not necessary since all samples were acidic) and with the "no treatment" indicator. To deionized water were added a small quantity of $NaHCO_3$ to obtain some alkalinity, and a quantity of HCl to lower pH below 7.0. Table 14 summarizes the results for "no treatment" (0) and three (3) and five (5) drops of base demand.

TABLE 14

Treatment of Acidic Samples Having Low Alkalinity

| Initial TA | Initial pH | 5 BD | 5 BD (color) | 3 BD | 3 BD (color) | 0 | 0 (color) |
|---|---|---|---|---|---|---|---|
| 50 | 7.0 | >8.0 | (8.2) | 7.5 | R | <7.0 | (6.9) |
| 50 | 6.82 | 7.8 | * | >7.1 | R | <7.0 | (6.8) |
| 50 | 6.75 | 7.5 | R | 7.0 | * | <7.0 | (6.7) |
| 40 | 6.63 | 7.3 | R | <7.0 | (6.9) | <7.0 | (6.7) |
| 40 | 6.41 | <7.0 | (6.8) | <7.0 | (6.7) | <7.0 | (6.5) |

For the last entry, two additional drops of base demand raised the pH to about 7.2, within the target range. It is evident that these less-buffered samples work well with three (3) and five (5) drops of base demand for pH as low as about 6.6.

The foregoing examples describe various features of the invention, which is an analytical system useful in determining concentration of one or more analytes in a liquid sample, and the effect on the concentration of said analyte caused by adding a defined amount of a particular substance to said liquid sample. The analytical system may be a wet chemistry or dry chemistry based system, as described supra.

The present invention can be used to test liquid samples from a host of different sources and for numerous different analytes. By way of example, in accordance with the invention, water from swimming pools, spas, boilers, cooling systems, aquaria, aquaculture, hydroponics, laboratory grade water, natural or industrial streams, reservoirs, etc. and the like can be tested for hydrogen ions (pH), bicarbonate, borate, carbonate, cyanurate, hydroxide, hypochlorite, hypochlorous acid, inorganic bases, monochloramine, dichloramine, organic chloramines, organic bases, phosphate, salts of organic acids, silicate, calcium, magnesium, biguanide, monopersulfate, persulfate, hypobromous acid, hypobromite, inorganic bromamines, organic bromamines, hydrogen peroxide, copper, iron, manganese, chloride, quaternary ammonium compounds, polyquaternary ammonium compounds, silver, or other recreational water constituents, benzotriazole, chlorine dioxide, chromium, fluoride, hydrazine, molybdenum, dissolved oxygen, ozone, phosphonate, phosphorus, polyacrylates, polymers, silica, sulfate, nitrite, N,N-diethylhydroxylamine, tannin, lignin, tolytriazole, zinc, or other industrial water constituents, aluminum, arsenic, barium, boron, cadmium, cobalt, cyanide, formaldehyde, iodine, lead, mercury, nickel, nitrogen, polychlorinated biphenyl, palladium, phenol, potassium, selenium, sulfide, surfactants, mono-, di-, and trivalent anions and cations, or other water constituents.

As used herein, "reagent" refers to a chemical moiety which reacts with an analyte to produce a detectable response, e.g., a colored reaction product. "Reagent system" refers to a mixture or other combination of (1) one or more reagents and (2) one or more solvent(s), stabilizer(s), surfactant(s), buffer(s), dye(s), and/or other components present with the reagent or reagents.

The method of the present invention comprises testing a liquid sample in which a detectable response is produced by reaction between an analyte in the liquid sample and at least one reagent. A liquid sample containing an analyte is contacted with one or more reagents capable of modifying the response to the concentration of the analyte in the liquid sample. As used herein, a modified (or changed) response refers to a response which represents or corresponds to a concentration of an analyte which is greater or lesser than the concentration initially present in the liquid sample. Reagents which modify the detectable response therefore can change or simulate a change in the concentration of the analyte in the liquid sample. By way of example, the one or more reagents can change or simulate a change in pH, total alkalinity, calcium hardness, total hardness, free chlorine, combined chlorine and /or total chlorine, bromine, cyanuric acid, copper, or iron in the liquid sample. The modified response can represent a corrective action, e.g., a user can compare the response to a standard to determine whether a particular corrective action is required.

The device of the present invention can be either in a "dry chemistry" form (e.g., an apparatus such as a "dipstick") or in wet-chemistry form, e.g., in which liquid samples are placed into test containers which contain one or more reagents (e.g., in the form of liquid, powder, tablet, or the like). Apparatus in accordance with the invention may comprise two or more absorbent pads, appended to a support means that is substantially inert with respect to the reagent (s).

A carrier matrix can be either porous, bibulous, non-porous or non-bibulous. Suitable bibulous matrices include filter paper, fleeces, sponge materials, cellulose, flocked material, wood, polymeric fibers (e.g., polypropylene), woven and non-woven fabrics, and the like. Non-bibulous matrices include glass fiber, polymeric films, and microporous membranes. Other types of matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally occurring polymers, such as cellulose acetate, polyvinyl chloride, polyacrylamide, polyacrylates, polyurethanes, crosslinked dextran, agarose, and other such crosslinked and non-crosslinked water-insoluble hydrophilic polymers. The carrier matrix can be of different chemical compositions or a mixture of chemical compositions. The carrier matrix also can vary in regards to smoothness and roughness combined with hardness and softness. As will be apparent to those skilled in the art, selection of the suitable matrix depends in part on the reagents used in a particular assay. For ease of handling, the matrix preferably has a handle, which can be formed, e.g. from hydrophobic materials such as cellulose acetate, polyethylene terephthalate, polycarbonate, or polystyrene.

The reagent compositions used in the invention may include a solvent such as water. When particular ingredients in the reagent composition have low water solubility, organic solvents, such as toluene, acetone, methanol, ethanol, isopropyl alcohol, ethylene glycol, propylene glycol, dimethyformamide, dimethylsulfoxide, acetonitrile, ethyl acetate, and similar solvents can be included in the carrier vehicle. The selection of a suitable organic solvent or solvents, in addition to water, to be included in the carrier of the reagent composition invention is within the capability of those skilled in the art of designing dry chemistry assays. The amount of organic solvent present in a reagent composition will vary, based upon the particular system being used. One of ordinary skill in the art can make this determination readily and easily.

The reagent systems of the invention can contain one or more surfactants, such as anionic, non-ionic, cationic, amphoteric, or zwitterionic surfactants. When used, a surfactant typically is present in the reagent composition in an amount 0.05 to about 1.5%, and more typically about 0.1% to about 1%, based on the weight of the composition. The surfactant not only can improve the ability of the test sample to wet the matrix, but also can improve the stability of the color transition of the one or more reagents in response to the analyte being tested. Surfactants also can help permit the reagent composition to assay for a broader range of analyte concentrations.

Non-limiting examples of non-ionic surfactants include ethoxylated polysorbate, e.g., polysorbate 20 through polysorbate 85; ethoxylated alcohol, e.g., $C_{10}$ to $C_{22}$ alcohol ethoxylated with about 10 to about 25 moles of ethylene oxide; ethoxylated phenol, e.g., ethoxylated octylphenol, nonylphenol, or dodecylphenol with about 8 to about 30 moles of ethylene oxide; polyethylene glycol, e.g., PEG-8 through PEG-40; polypropylene glycol, e.g., PPG-9 through PPG-34; ethylene glycol-propylene glycol copolymer, e.g., poloxamer, polybutylene glycol, as well as others, and mixtures of these may also be used.

Anionic surfactants are well known, and include fatty acids, salts of fatty acids, ethoxylated fatty acids, and salts of ethoxylated fatty acids. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, alkyl ether sulfosuccinates, sarcosinates, octoxynol phosphates, nonoxynol phosphates, taurates, fatty taurides, sulfated monoglycerides, fatty acid amido polyoxyethylene sulfates, and isothienates, or mixtures of salt thereof.

The reagent systems of the present invention may, but need not contain, a buffer. Non-limiting examples of buffers include citric acid, polycarboxylic acids, phosphate, borate, acetate, "GOOD" buffers and mixtures thereof. The reagent systems also can contain one or more stabilizers, such as acetonitrile as described in U.S. Pat. No. 4,290,773, and /or inhibitor systems including polymerizable or cross-linkable water-soluble polymers, epoxide/polyamine mixtures, water-reactive polyisocyanates, hydroxyl ion-polymerizable acrylate and substituted acrylate esters, polyvinyl alcohol mixtures with various metal compounds or with polyphenolic compounds, and various others as described in U.S. Pat. No. 4,038,485.

It will be understood that the examples and embodiments described in this application are exemplary, and should not be deemed limitative of the invention as described and claimed.

The terms and expressions which have been employed are used as terms of description and not of limitation and there is no intention in the use of such terms and expressions of excluding any equivalents of the features shown and described or portions thereof it being recognized that various modifications are possible within the scope of the invention.

I claim:

1. An apparatus useful in determining effect on concentration of an analyte in a liquid sample of a change in said liquid sample, comprising:
   (i) a first, solid phase reagent system which indicates concentration of said analyte in said liquid sample, and
   (ii) a second, solid phase reagent system which indicates or simulates effect of a defined change on said analyte.

2. The apparatus of claim 1, wherein said first and second solid phase reagent systems comprise reagent pads, each of which contains a reagent system, wherein said reagent pads are fixed to a solid, inert carrier.

3. The apparatus of claim 1, wherein said second, solid phase reagent system indicates or simulates an increase in said analyte.

4. The apparatus of claim 1, wherein said second, solid phase reagent system indicates or simulates a decrease in said analyte.

5. The apparatus of claim 3, further comprising a third, solid phase reagent system which indicates or simulates a decrease in said analyte.

6. The apparatus of claim 1, further comprising a separate reference table for analysis of signals generated in said first and second solid phase reagent systems.

7. The apparatus of claim 1, wherein said analyte is total alkalinity, calcium hardness total hardness, pH, total chlorine, combined chlorine, free chlorine, bromine, cyanuric acid, copper or iron.

8. The apparatus of claim 1, wherein said liquid sample is a sample of swimming pool water, spa water, boiler water, cooling water, water for aquaculture, or drinking water.

9. Apparatus useful in determining if concentration of an analyte in a liquid sample exceeds a defined value, comprising:
   (i) a first solid phase reagent system which provides a detectable signal upon contact with said liquid sample that is indicative of said analyte in said liquid sample, and
   (ii) a second solid phase reagent system which provides a detectable signal indicative of said defined value.

10. The apparatus of claim 9, wherein said first and second solid phase reagent systems are contained in separate, first and second reagent pads which are fixed to a solid, inert carrier.

11. The apparatus of claim 9, wherein said analyte is total chlorine.

12. The apparatus of claim 9, wherein said first solid phase reagent system provides a detectable signal indicative of total chlorine in said liquid sample, and said second solid phase reagent system provides a detectable signal indicative of a defined amount of combined chlorine and the amount of free chlorine in said sample.

13. The apparatus of claim 1, comprising a plurality of first and second solid phase reagent systems, each member of said plurality of first and second solid phase reagent systems being useful in determining a different analyte.

14. A method for determining effect on concentration of an analyte in a liquid sample of a change in said liquid sample, comprising contacting the apparatus of claim 1 to a liquid sample, and comparing signal generated in (i) and (ii) to reference values.

15. A method for determining if the amount of combined chlorine in a sample exceeds a defined value, comprising contacting the apparatus of claim 12 to a liquid sample, and comparing signal generated in (i) and (ii) to a reference value to determine if the amount of combined chlorine in said sample exceeds said defined value.

16. Reagent system useful in determining effect on concentration of an analyte in a liquid sample of a change in said liquid sample, comprising:
   (i) a first solubilized or solubilizable reagent system which indicates concentration of said analyte in said liquid sample, and
   (ii) a second solubilized or solubilizable reagent system which indicates or simulates effect of a defined change on said analyte.

17. The reagent system of claim 16, wherein (i) and (ii) are in solubilized form.

18. The reagent system of claim 16, wherein (i) and (ii) are in solubilizable form.

19. The reagent system of claim 16, further comprising a separate container means for combination of each of (i) and (ii) with said liquid sample.

20. The reagent system of claim 16, wherein (ii) indicates or simulates an increase in said analyte.

21. The reagent system of claim 16, wherein (ii) indicates or simulates a decrease in said analyte.

22. The reagent system of claim 20, further comprising a third reagent system which indicates or simulates a decrease in said analyte.

23. The reagent system of claim 16, wherein said analyte is total alkalinity, calcium hardness, total hardness, pH, total chlorine, free chlorine, combined chlorine, bromine, cyanuric acid, copper, or iron.

24. The reagent system of claim 16, wherein said liquid sample is swimming pool water, spa water, boiler water, cooling water, water for aquaculture, or drinking water.

* * * * *